United States Patent [19]

Grassetti

[11] Patent Number: 4,521,425

[45] Date of Patent: Jun. 4, 1985

[54] AGENTS AFFECTING THE PRODUCTION OF HORMONES IN LIVING MAMMALS

[76] Inventor: Davide R. Grassetti, 26 Northgate Ave., Berkeley, Calif. 94708

[21] Appl. No.: 528,226

[22] Filed: Aug. 31, 1983

Related U.S. Application Data

[63] Continuation-in-part of Ser. No. 307,237, Nov. 2, 1981, abandoned.

[51] Int. Cl.$^3$ ............................................ A61K 31/455
[52] U.S. Cl. .................................................... 514/350
[58] Field of Search ........................................ 424/266

Primary Examiner—Jerome D. Goldberg

[57] ABSTRACT

This invention relates to a method for treating a mammal to decrease its blood cortisol level with the administration of 6-mercaptonicotinic acid.

2 Claims, No Drawings

AGENTS AFFECTING THE PRODUCTION OF HORMONES IN LIVING MAMMALS

The present application is a continuation in part of my application Ser. No. 307,237, filed Nov. 2, 1981 (now abandoned).

It has been discovered that administration of a mercaptopyridine carboxylic acid to human subjects causes a substantial decrease of the level of blood cortisol, a key glucocorticoid steroid hormone.

This decrease is brought about upon oral administration of 6-mercaptonicotinic acid (6MNA), and no adverse side-effects have been observed.

The administration of an agent reducing the level of blood cortisol is useful to treat hypercortisolism. An increased secretion of cortisol by adrenal glands, however caused, produces Cushing's syndrome, whose main features are hyperglycemia (or even diabeles mellitus), obesity, hirsutism and osteoporosis.

It is desirable to reduce the blood level of cortisol to treat hypercortisolism.

EXAMPLE 1

Intraperitoneal Administration of 6-Mercaptonicotinic Acid to Mice

Each of 10 healthy Swiss mice were injected intraperitoneally 1 mg per day (dissolved in 0.1 ml of distilled water) of the sodium salt of 6MNA, for 7 consecutive days. This corresponds to a daily dose of 40 mg/kilo. No adverse effects were observed.

EXAMPLE 2

Oral Administration of 6-Mercaptonicotinic Acid to Mice

Each of 12 healthy mice was administered orally 6MNA mixed with the diet. The regular mouse chow was ground to a fine powder, mixed with the appropriate amount of 6MNA, and, after addition of a sufficient amount of distilled water, reshaped into pellets and dried. The amount of 6MNA in the diet was 1 mg per gram of chow, corresponding to an average daily uptake of 120 mg per kilo. This diet was continued for 30 consecutive days. A control group of 12 mice receiving the normal diet without additions was also observed. No adverse effects were observed, and no differences were found vetween test and control groups.

EXAMPLE 3

Subcutaneous Administration of 6-Mercaptonicotinic Acid to Cows

Three cows were given each an injection of 1.5 gram (in 8 ml water containing the stoichiometric amount of sodium bicarbonate to neutralize the 6MNA). This corresponds to 3 mg/kilo. No harmful effects were noted.

EXAMPLE 4

Administration of 6-Mercaptonicotinic Acid to Woman

6-Mercaptonicotinic acid (160 milligrams) was administered to a 45-year-old woman, immediately after withdrawal of the zero-time blood sample. Blood samples were taken 3, 6, and 9 hours after administration of the compound. SMA II and hemochrome values were not significantly modified in this period. The cortisol levels were as follows:

| Time | 0 | 3 | 6 | 9 Hours |
| --- | --- | --- | --- | --- |
| Blood Cortisol | 10.50 | 8.00 | 7.00 | 10.80 mcg/dl |

The cortisol level decreased 23.8% after 3 hours, and 33.3% after 6 hours.

EXAMPLE 5

Administration of 6-Mercaptonicotinic Acid to Woman

6-Mercaptonicotinic acid (160 mg) was administered orally to a 30-year-old woman, immediately after withdrawal of the zero-time blood sample. Blood samples were then taken 3 and 6 hours after administration of the compound. SMA II and hemochrome values were not significantly modified in this period. The cortisol levels were as follows:

| Time | 0 | 3 | 6 Hours |
| --- | --- | --- | --- |
| Blood Cortisol | 30.00 | 13.00 | 21.00 mcg/dl |

The cortisol levels decerased 56.7% after 3 hours.

Example 6

Administration of 6-Mercaptonicotinic Acid to Man

6-Mercaptonicotinic acid (160 mg) was administered orally to a 38-year-old man, immediately after withdrawal of the zero-time blood sample. Blood samples were then taken 3, 6, and 9 hours after administration of the compound. SMA II and hemochrome values were not significantly modified in this period. The cortisol levels were as follows:

| Time | 0 | 3 | 6 | 9 Hours |
| --- | --- | --- | --- | --- |
| Blood Cortisol | 13.50 | 7.50 | 11.50 | 12.50 mcg/dl |

The cortisol level decreased 44.4% after 3 hours.

EXAMPLE 7

Administration of 6-Mercaptonicotinic Acid (sodium salt) to woman

6-Mercaptonicotinic acid (160 mg) dissolved in water together with a slight stoichiometric excess of sodium bicarbonate, was administered orally to a 28-year-old woman, immediately after withdrawal of the zero-time blood sample. Blood samples were taken 3, 6, and 9 hours after administration of the compound.

SMA II and hemochrome values were not significantly modified in this period.

The cortisol levels were as follows:

| Time | 0 | 3 | 6 | 9 Hours |
| --- | --- | --- | --- | --- |
| Blood Cortisol | 22.00 | 12.00 | 16.70 | 22.20 mcg/dl |

The cortisol level decreased 45.5% after 3 hours.

EXAMPLE 8

Administration of 6-Mercaptonicotinic Acid (sodium salt) to Man

6-Mercaptonicotinic Acid (160 mg) dissolved in water together with a slight stoichiometric excess od sodium bicarbonate, was administered orally to a 46- year-old man, immediately after withdrawal of the zero-time blood sample. Blood samples were taken 3, 6, and 9 hours after administration of the compound. SMA II and hemochrome values were not significantly modified in this period.

The cortisol levels were as follows:

| Time | 0 | 3 | 6 | 9 Hours |
|---|---|---|---|---|
| Blood Cortisol | 13.90 | 6.90 | 7.90 | 11.30 mcg/dl |

The cortisol level decreases 50.4% after 3 hours.

It is seen from Examples 4, 5, 6, 7, and 8 that decrease of the blood level of cortisol occurs 3 hours after oral administration of 6-mercaptonicotinic acid or its sodium salt (average decrease: 44.1%); after this time the cortisol level eventually increases approaching the original value. It is expected that repeated administration of 6MNA will lower the cortisol level for longer periods of time.

The alkali metal salts and the lower alkyl esters ($C_1$ to $C_3$) of the mercaptopyridine carboxylic acids may be administered instead of the acids themselves to obtain substantially equivalent reductions in blood cortisol levels.

I claim:

1. The method of treating a mammal to decrease its blood cortisol level which comprises administering to a mammal in need of such treatment an amount of 6-mercaptonicotinic acid, its alkali metal salts or its lower alkyl esters effective to reduce the blood cortisol level of said mammal.

2. The method of claim 1 wherein the amount administered is in the range 0.1–50 mg/kilo.

* * * * *